United States Patent [19]

Cobbold et al.

[11] Patent Number: 4,841,025

[45] Date of Patent: Jun. 20, 1989

[54] ANTIBODY PREPARATIONS

[75] Inventors: Stephen P. Cobbold; Herman Waldmann, both of Cambridge, England

[73] Assignee: National Research Development Corporation, London, United Kingdom

[21] Appl. No.: 171,164

[22] Filed: Mar. 21, 1988

Related U.S. Application Data

[63] Continuation of Ser. No. 624,205, Jun. 25, 1984, abandoned.

[51] Int. Cl.⁴ .................... A61K 39/395; C07K 3/12
[52] U.S. Cl. ........................ 530/387; 530/388; 530/412; 530/413; 530/808; 435/68; 435/240.27; 424/85.8; 935/107; 935/110
[58] Field of Search ............... 530/387, 389, 412, 413, 530/808; 436/548; 435/68, 240.27; 424/85; 935/107, 110

[56] References Cited

FOREIGN PATENT DOCUMENTS 0068763 6/1982 European Pat. Off. .

OTHER PUBLICATIONS

Galfré et al., Nature, 277 (1979), 131–3.
Peabody, Ely, and Edmundson, Biochemistry, 1980, 19, 2827–2834.
U. Raso and T. Griffin, Cancer Research, 1981, 2073–2076.
S. P. Cobbold & H. Waldmann, Therapeutic Potential of Monovalent Monoclonal Antibodies, Nature, 1984, vol. 308, No. 5958, pp. 460–462.
M. J. Glennie & G. T. Stevenson, Univalent Antibodies Kill Tumour Cells in Vitro and in Vivo, Nature, vol. 295, Feb. 1982, p. 712.
G. T. Stevenson, M. J. Glennie, J. Gordon, The Killing of Lymphoma Cells by Univalent Derivatives of Tumor—Specific Antibody, B & T Cells Tumor, 1982, p. 459.
G. T. Stevenson and D. Straus, Specific Dimerization of the Light Chains of Human Immunoglobulin, Biochemical Journal, 1984, p. 375.

Primary Examiner—Christine M. Nucker
Attorney, Agent, or Firm—Nixon & Vanderhye

[57] ABSTRACT

A monoclonal antibody preparation having a single binding activity, which activity is in respect of a cell surface antigen, comprises IgG antibody molecules in which only one of the two light chains will bind to said antigen, the proportion of such antibody molecules being enhanced relative to IgG antibody molecules having two light chains which will bind to said antigen to thereby produce an enhancement of the binding activity of the preparation. Such preparations containing predominatly "monovalent antibodies" are of particular value in the areas of transplantation immunity, the treatment of neoplastic disease and cell sorting.

15 Claims, 2 Drawing Sheets

ANTIBODY PREPARATIONS

This application is a continuation of Ser. No. 624,205, filed June 25, 1984, now abandoned.

This invention relates to antibodies and in particular to novel preparations of antibodies.

Antibodies are generally bivalent, or less often multi-valent, and this bivalency enhances the strength of attachment of the antibody to cell surfaces. However, the bivalency of the antibody sometimes induces a target cell to undergo antigenic modulation thereby providing a means whereby the cell can avoid the cytotoxic agents, effector cells and complement, which are involved in the cell-antibody interaction. As a means of preventing such modulation, other workers have utilised antibodies raised by classical procedures from which one Fab fragment has been removed and which are thus monovalent.

Using a quite different approach, we have developed a novel preparation of antibodies which possesses the advantages of monovalency without involving any necessity for the cleavage of immunoglobulins and the separation of the cleavage products. At the same time, this new type of antibody preparation is accessible through the application of hybridoma technology, and indeed is limited to monoclonal antibodies produced by this technology, thereby providing a particularly convenient route to monovalent antibodies.

According to the present invention a monoclonal antibody preparation having a single binding activity, which activity is in respect of a cell surface antigen, comprises IgG antibody molecules in which only one of the two light chains will bind to the antigen, the proportion of such IgG antibody molecules being enhanced relative to IgG antibody molecules having two light chains which will bind to the antigen.

Such antibodies which have only one light chain which will bind to the cell surface antigen are referred to herein as "monovalent antibodies" whilst those having two such chains are referred to as "bivalent antibodies". The "monovalent antibodies" of the present invention, which have a single binding activity, are quite distinct from the antibodies described in European Patent Application No. 0068763, which have two binding activities, and which may be termed "heterobivalent antibodies" in contrast to the bivalent antibodies just referred to which are "homobivalent antibodies".

It will most usually be the case that a similar pair of identical heavy chains specific for the cell surface antigen is present in both the monovalent and the homobivalent IgG antibody molecules. However, whilst the latter type of molecule contains two light chains specific for the antigen, the former type usually contains a first light chain which is specific for the antigen and a second light chain which is non-specific for the antigen. The combination of a specific heavy chain with a specific light chain forms an effective binding site for the cell surface antigen, whilst the combination of a specific heavy chain and a non-specific light chain forms an inactive site. It will be appreciated that it is also possible for both of the light chains to be specific for the cell surface antigen in question but for only one of the heavy chains to be specific for this antigen thereby again producing only one active binding site, but mixtures containing such monovalent antibodies are generally less easy to fractionate and these antibodies are accordingly of less interest.

The expression "an enhanced proportion" is used above to indicate that the proportion of monovalent antibodies to bivalent antibodies has been increased as compared with that present in the mixture of antibodies as originally produced by the hydridoma from which the antibodies derive. For the production of a monoclonal antibody mixture for fractionation to provide monovalent antibodies it is preferred to use a hybridoma which expresses two identical specific heavy chains and one specific and one nonspecific light chain. The original proportion of monovalent: bivalent antibodies produced by such a hybridoma may vary over quite a wide range for individual hybridomas but the most usual ratio is generally thought to be about 2:1, an average monoclonal antibody mixture from such a hybridoma thus containing, apart from aggregates, approximately 50% of monovalent antibodies and 25% of each of antibodies containing two non-specific light chains and antibodies containing two specific light chains. Although some deviation from these figures will occur in individual cases, both in favour of the monovalent antibodies and in favour of the bivalent antibodies, it is believed that the proportion of monovalent antibodies to bivalent antibodies as produced by a hybridoma never achieves a ratio of as high as 10:1, which ratio corresponds, on the basis of the 2:1 ratio discussed above, to a 5-fold enhancement relative to the monovalent antibodies.

Accordingly, the present invention includes an antibody preparation as defined hereinbefore in which the proportion of antibodies which consist of IgG in which only one of the two light chains will bind to the cell surface antigen in relation to antibodies which consist of IgG in which both light chains will bind to the antigen is 10:1 or more.

It will be appreciated that with certain individual hybridomas a 5-fold enhancement of the monovalent antibody: bivalent antibody ratio produced by the hybridoma may give a ratio of less than 10:1, for example 5:1, in view of a lower than normal initial proportion of monovalent antibody. However, experiments have shown that in practice, for the full expression of the advantages of the present invention, it is preferred to use a proportion even higher than 10:1. Conveniently, the proportion may be 25:1, 50:1 or especially 100:1 or more (corresponding to a 12.5, 25 and 50-fold enhancement relative to a 2:1 ratio) and the enhanced effect produced may even justify an increase in the proportion of the monovalent antibodies to a figure of as much as 500:1 or even 1000:1 or more (corresponding to a 250 and 500-fold enlargement relative to a 2:1 ratio).

The present invention thus further comprises monoclonal antibodies having a single binding activity, which activity is in respect of a cell surface antigen, which consist of IgG in which only one of the two light chains present will bind to said antigen, said monoclonal antibodies being in admixture with other monoclonal antibodies which consist of IgG in which both light chains will bind to said antigen in a proportion of 10:1 or more, for example 100:1 or more, for example up to 1000:1. In particular said first monovalent type of antibodies may conveniently be substantially free from said second bivalent type of antibodies.

The production of a monoclonal antibody preparation in which the proportion of monovalent antibodies is enhanced is considerably facilitated when there is a serological distinction between the first light chain and the second light chain of the monovalent antibodies.

This distinction may be of various types but in particular may consist in a different of allotype, of idiotype or of species. It will be appreciated, therefore, that in a preferred aspect the present invention includes a monoclonal antibody preparation having activity against a cell surface antigen which comprises IgG antibody molecules having two identical heavy chains specific for the antigen, a first light chain specific for the antigen and a second light chain serologically distinct from the first which is non-specific for the antigen, the proportion of such antibody molecules being enhanced relative to IgG antibody molecules having two heavy chains and two light chains specific for the antigen.

Hybridomas acting as a source of monovalent antibodies according to the present invention may be obtained in various ways. Certain myelomas express a light chain characteristic of the source of the myeloma, more particularly of the individual from which the myeloma derives, and it is generally the case that hybridomas obtained from such a myeloma will express not only a light chain specific for the antigen in question but also the light chain characteristic of the myeloma. Other myelomas, although not expressing a light chain themselves, will nevertheless impart to hybridomas derived therefrom the ability to express a light chain characteristic of the myeloma. Such a property of imparting a light chain to a hybridoma is generally regarded as a disadvantage. Thus, the myeloma YB2/3.-0.Ag.20 of UK Patent Application No. 8120621, published under the number GB 2079313A, is described as being an improvement on the myeloma from which it is derived, the myeloma Y3-Ag 1.2.3 of UK Pat. No. 2039948, in that, unlike the original myeloma, it does not to impart hybridomas derived therefrom a light chain characteristic of the myeloma. The present invention is based in part upon an appreciation of the fact that the ability of such myelomas as Y3-Ag 1.2.3 to impart a light chain to the hybridoma can be an advantage in the context of producing hybridomas acting as a source of monovalent antibodies. The Y3-Ag 1.2.3 myeloma expresses a kappa light chain which is characteristic of the allotype of the Lou rat straing, Y3-Ag 1.2.3 having been originally derived from a rat of this strain. The myeloma has been deposited with the CNCM at the Institut Pasteur in Paris under the number I-078 in connection with the UK patent and other patents, such as the European Pat. No. 0014519. Other specific examples of myelomas which may be used in the present invention are the mouse P3-X63-Ag8 and NS1/1-Ag4-1 myelomas which do not themselves express a light chain, but on fusion to produce a hybridroma will impart to that hybridoma the ability to express a mouse light chain characteristic of the derivation of the myeloma. These myelomas are available, inter alia, from the American Type Culture Collection (ATCC), Maryland, USA, having been deposited as P3-X63-Ag8U under the number CRL 1597 and as P3/NS1/1-Ag4-1(NS-1) under the number TIB 18.

A preferred form of monoclonal antibody preparation according to the present invention is obtained by starting with any myeloma which will express a light chain and fusing this with immunocytes sensitized to the cell surface antigen in question to produce a hybridoma. Such a hybridoma will generally express two identical heavy chains derived from the immunocytes together with one specific light chain derived from the immunocytes and one nonspecific light chain derived from the myeloma. The myeloma may be derived from any animal species (the word animal being used in its broad sense to cover mammals, including humans, and also birds). However, most commonly a mouse or rat myeloma, or a human myeloma where one of a suitable nature is available, is preferred. The technique of hybridoma production from a myeloma by the fusion of myeloma cells with immunocytes, for example spleen cells, is by now very well documented in the literature and is described, for example, in the specification of the UK Pat. No. 2039948 relating to Y3-Ag 1.2.3 which has been referred to hereinbefore. Two points should, however, be stressed. Firstly, in the preferred case where the two different types of light chain present in the monoclonal antibodies expressed by the hybridoma are serological distinct, the immunocytes should be derived from an individual that is immunologically different from that from which the light chain expressed by the myeloma originally derives. It may be the case that the two individuals are of a different species or of immunologically different types of the same species. Thus the Y3-Ag 1.2.3 myeloma referred to above, which is derived from a Lou strain of rat, may for example be fused with immunocytes from any mouse or from an immunoligically different type of rat such as an AO or DA strain of rat. Secondly, the present invention requires the monoclonal antibody to be of the IgG type in view, for example, of the multivalency of the IgM type of immunoglobulin. Therefore, when screening the fusion products for suitable hybridomas it is necessary to ensure that these hybridomas produce an IgG monoclonal antibody.

It is possible, however, to use various alternative approaches to a myeloma/immunocyte fusion in order to effect a similar combination of tumour character and the desired specificity in a hybridoma. Firstly, it is possible, instead of fusing a light chain-producing myeloma with immunocytes specific to a cell surface antigen, to fuse with the immunocytes a hybridoma which expresses a myeloma-derived light chain and to separate from the fusion products a hybridoma which expresses both this non-specific light chain and a light chain specific for the antigen. Alternatively, it is possible to start with a hybridoma of suitable specificity which does not, however, express a myeloma-derived light chain, to fuse this hybridoma with either a light chain-producing myeloma or a light chain-producing hybridoma, and to separate from the fusion products a hybridoma which expresses both a specific light chain and this non-specific light chain.

Moreover, it will be appreciated that although the non-specific light chain present in monoclonal antibodies according to the present invention is most conveniently derived from a myeloma either directly or through a hybridoma, this does not have to be the case. Thus, as an alternative to fusing a hybridoma expressing only specific light chains with a myeloma or hybridoma as a source of a non-specific light chain, it is possible to effect the fusion of this hybridoma with another source of a non-specific light chain, for example spleen or other immunocyte cells (which do not need to be specifically sensitized), or lymphocytes (which again do not need to be specifically sensitized) which have been transformed with Epstein-Barr virus, this alternative approach being of particular interest in relation to human cells in view of the limited availability of suitable human myelomas. Other procedures utilising lymphocytes transformed by Epstein-Barr virus, which are however of lesser interest, may involve the fusion of specifically sensitized lymphocytes with spleen or other immunocyte cells which are not specifically sensitized or with a myeloma or hybridoma in order to derive a non-specific light chain from the non-lymphocyte partner of the fusion. Such alternative procedures to a myeloma/ immunocyte fusion, and other possible variations which will be apparent to the man skilled in the art, may all be effected using conventional procedures described in the art.

The selected hybridoma may be used to prepare monoclonal antibodies by an in vitro or in vivo method, these methods again being well described in the literature, for example in the specification of UK Pat. No. 2039948. The monoclonal antibodies thus obtained will contain monovalent antibodies but these will be in admixture with bivalent antibodies containing two specific light chains and with inactive antibodies containing two non-specific light chains. In order to produce monoclonal antibodies according to the present invention it is necessary to remove at least a part of the bivalent antibodies present in the mixture. The inactive antibodies may also be removed in part or substantially as a whole if desired, although this is optional since the inactivity of these antibodies allows them to be retained in admixture with the monovalent antibodies providing the proportion of bivalent antibodies has been lowered.

Various alternative methods exist for separation of the bivalent antibodies from the monovalent antibodies. One convenient technique involves the use of affinity chromatography utilising an antibody, particularly a monoclonal antibody, with an allotype, idiotype or species affinity for the second, non-specific, light chain in which it is serologically distinct from the first light chain. Such a second light chain is of course present in the monovalent and inactive antibodies but not in the bivalent antibodies. The affinity may vary from being exclusive to only preferential and whilst the latter is acceptable the former is clearly more desirable if such an antibody is available. Examples of antibodies which may be used are antibodies against the kla and klb light chain rat allotypes and anti-mouse IgG antibodies where the non-specific light chain is derived from a mouse, for example from a mouse myeloma, and the other light chain and the heavy chains from a rat, for example from rat spleen cells, or anti-rat IgG antibodies in the opposite case. Instead of anti-mouse IgG antibodies, the material protein A referred to below may be used. On treatment of the monoclonal antibody mixture produced by the hybridoma with the affinity material, the monovalent and inactive antibodies which each contain a non-specific light chain will bind more strongly to the material than the bivalent antibodies which contain no such light chain and which will therefore remain unbound or will be only weakly bound.

The anti-allotype, anti-idiotype or anti-species antibody may itself conveniently be purified before use by affinity chromatography, for example on an anti-rat IgG column or the like as appropriate. An alternative approach of some interest involves the use of an alternative form of derivatised support material reactive towards a particular type of protein. Thus protein A (from *S. aureus*) may be coupled to a support material such as Sepharose using some form of bifunctional coupler to provide a material to which mouse IgG will bind strongly and which may be used as an alternative to anti-mouse IgG in purifying a mouse derived antibody.

The affinity material for production of a monoclonal antibody preparation according to the present invention may comprise the anti-allotype, anti-idiotype or anti-species antibody attached to one of a variety of forms of polymeric material suitable as the basis of an immunoadsorbent. Such materials are described in the literature in relation to gel filtration chromatography of proteins and include carbohydrate materials based upon dextran, agar or agarose and also polyacylamide based materials, cross-linking conveniently being used to impart the required degree of exclusion of molecules depending upon size and shape. Examples of such materials are marketed under the trade names Sepharose (agarose based), Sephadex (dextran based) and Sephacryl (allyldextran based with cross-linking by an acrylamide derivative). The antibody may be attached to the support material through the use of one of various methods described in the literature by which proteins or other materials may be attached to insoluble solid phase supports of use in affinity chromatography. The chemical reactions described effect covalent bond attachment, but by a non-denaturing methodology so that destruction of the attached labile substances is minimised. Examples of suitable linking agents include the 1,4-bis(2,3-expoxypropoxy)-butane type of linking agent and particularly cyanogen bromide, these linking agents being suitable for use with non-derivatised support materials such as those carbohydrate materials specified above. Alternatively, derivatised support materials may be used with other linking agents or derivatised support materials containing a reactive functional group may be used without a separate linking agent. One particularly convenient approach of this type involves the use of the cyanogen bromide activated Sepharose material marketed by Pharmacia.

The details of the affinity separation technique will vary depending particularly upon the degree of affinity of the affinity material for the non-specific light chain. Some general guidance, may however, be given. The affinity material is exposed to the anti-cell surface antigen monoclonal antibody mixture to be fractionated under conditions suitable to effect binding of the desired fractions, for example by incubation for 2 hours at 4° C. with continuous mixing, it often being suitable to effect mixture of the affinity material and the monoclonal antibody mixture in double strength phosphate buffered saline (PBS) to reduce nonspecific binding and antibody aggregation. Such mixing is more conveniently effected before the affinity material is introduced into a column. For elution of a column of the monoclonal antibody mixture-adsorbed affinity material, it is preferred initially to use a lower strength eluant to remove any monoclonal antibody not containing a non-specific light chain which may have become attached to the material, particularly where the antibody which comprises the active component of this affinity material only shows a preferential and not an exclusive affinity for this light chain. A mixture of monovalent and inactive monoclonal antibodies may then be removed from the column using full strength eluant. Thus, for example, a first elution with 0.1M acetate buffer of pH 4.0 containing 0.5M NaCl and a second elution with 1.0M glycine/HCl of pH 2.5 may often be suitable.

In one preferred aspect, therefore, the present invention includes a process for fractionating a monoclonal antibody mixture having activity against a cell surface antigen and containing a first type of IgG antibody molecule having a first light chain which is specific for the cell surface antigen and a second light chain serologically distinct from the first which is non-specific for the antigen and a second type of IgG antibody molecule having two of said first light chains, which comprises contacting the mixture with an affinity column carrying antibody directed against an allotype, idiotype or species characteristic of said second light chain in which it is serologically distinct from said first light chain to thereby effect a separation, which may be partial or complete, of said first type of IgG molecule from said second type of IgG molecule. It will be appreciated, however, that alternative procedures may be used for the separation of fractions in the monoclonal antibody mixture than the affinity chromatography procedures based upon a serological distinction described above. These alternatives include methods such as ion exchange chromatography and chromatofocussing which will effect a separation on the basis of the light chain isoelectric point and thus are applicable to the separation of IgGs which differ in one or both of their light chains, with the appropriate physical distinction between the differing light chains. Such procedures provide a route to monovalent monoclonal antibodies which contain a reduced proportion of or are substantially free not only from the bivalent antibodies but also from the inactive antibodies.

Monovalent monoclonal antibodies prepared as described above may contain aggregates and aggregates may also be formed on storage. Before using the antibodies such aggregates may conveniently be substantially removed either by centrifugation or by an alternative procedure where centrifugation leads to co-precipitation of non-aggregate antibodies.

Although the present invention may be widely applied to monoclonal antibodies specific for differing forms of surface antigen, especially in the context of various diagnostic and therapeutic (including prophylactic) applications, it is of particular value in certain such specific contexts, for example the areas of fertility control and particularly of transplantation immunity and the treatment of neoplastic disease. In many cases, monoclonal antibodies directed against human cell surface antigens are of particular interest although in certain areas such as fertility control monoclonal antibodies directed against non-human mammalian cell surface antigens may also be of particular interest.

The area of transplantation immunity involves the use of monovalent monoclonal antibodies having activity against lymphocytes, usually human lymphocytes, and particularly the T-lymphocytes. Antibodies of especial value are those which will fix human complement such as the antibodies produced by the hybridoma described by Cobbold et al in Journal of Cellular Biology, Supplement 7A, 1983, 72. Such antibodies are of value in graft procedures in various contexts, for example the removal of lymphocytes from bone marrow grafts to reduce donor/host interactions and the reduction of blood lymphocyte levels in the host for a similar purpose. Another use in this area involves the treatment of a patient's own bone marrow for removal of leukaemic lymphocytes and subsequent transplantation back into the patient.

In general, however, the treatment of neoplastic disease involves the use of monovalent monoclonal antibodies having activity against antigens specifically associated with the surface of neoplastic cells, various antibodies against tumour associated antigens being described, for example, in the specification of U.S. Pat. No. 4,172,124. The monovalent monoclonal antibodies may be used either as such or in conjunction with a cytotoxic agent which is bound thereto and thereby targeted to the neoplastic cells.

The applications of the present invention described above all depend on the use of the antibodies for the destruction of specific cells and employ the avoidance of antigenic modulation through the use of monovalent rather than homo-bivalent antibodies to thereby fully utilise the toxic action of effector cells and particularly the complement. A further use of monoclonal antibodies according to the present invention, which in this case does not rely upon a toxic effect, occurs in various blood test procedures. In techniques such as immunofluorescence cell sorting it is desirable to achieve a high level of binding of monoclonal antibodies to blood cells without concomitant agglutination which can be a major cause of misleading results. By providing monovalent monoclonal antibodies for use in such procedures, cross-binding between cells can be reduced. The specificity of antibodies used in this application of the invention can be against various surface antigens on various blood cells including erythrocytes, lymphocytes and other cells as detailed in the Table of Example 3 (PMN is an abbreviation for polymorphonuclear neutrophils.) By using one or more monovalent antibodies in conjunction with conventional cell sorting procedures it is possible to achieve significant improvements in sorting cells into different types. A common approach is to utilise a monovalent antibody directed against a cell surface antigen which occurs on different blood cells at differing levels, one example of such an antibody being obtained from the hybridoma YBM 34.3.6 described in Example 1 which is specific for a heat stable surface antigen occurring on many blood cell types.

The applications of monovalent antibodies according to the present invention are diverse and the antibodies will be formulated for use in a way depending on the particular application in accordance with conventional procedures in the art. Usually, however, the antibodies will be formulated in the presence of a physiologically acceptable diluent or carrier, often the former, for example in phosphate buffered saline.

It will be appreciated that the present invention also includes methods of using monoclonal antibody preparations as defined hereinbefore in the ways described above, whether as pharmaceutical compositions, or otherwise.

The invention is illustrated by the following Examples.

EXAMPLE 1

Preparation of Monovalent Monoclonal Antibodies against a Blood Cell Antigen

The hybridoma designated YBM 34.3.6 is prepared by the fusion of the rat myeloma lijne Y3-Ag 1.2.3 and spleen cells from DA rats immunized with CBA/Ca mouse bone marrow cells as described by Hoang et al, Blood, 1983, 61, 580 (in which paper the simpler designation YBM 34.3 is employed for this hybridoma). For the production of a mixture of forms of YBM 34.3.6 monoclonal antibodies (IgG2c isotype) which are specific for a heat stable antigen present in mice on the surface of many blood cell types at differing levels, cells of the hybridoma YBM 34.3.6 are cultured as described by Hoang et al.

Following removal of the cells, culture supernatant containing a mixture of forms of YBM 34.3.6 monoclonal antibodies is centrifuged at 10,000 r.p.m. for 30 minutes using a MSE HS25 centrifuge and the separated product is applied in double strength phosphate buffered saline (PBS) to Sepharose gel carrying MRC-OX12 monoclonal antibody[1] (the preparation of which gel is described in a footnote to this Example) at approximately 500 µg per ml of packed, wet gel. The mixture of YBM 34.3.6 antibody and MRC-OX12-Sepharose gel is incubated at 4° C. for 2 hours with constant rotation. The gel is then washed thoroughly with double strength PBS and is loaded into a glass column for elution.

[1]This antibody binds effectively with the Ye-Ag 1.2.3. myeloma derived kla allotype light chain-containing monoclonal antibodies but not with the DA rat derived klb allotype light chain-containing monoclonal antibodies.

The column of gel is eluted with 0.1M acetate buffer of pH 4.0 containing 0.5M NaCl to elute any antibody molecules containing two specific light chains which may have been weakly bound to the gel and also to elute aggregated material which will similarly only be weakly bound. Following this, the column of gel is eluted with 1.0M glycine/HCl of pH 2.5 in order to remove from the column a mixture of antibody molecules containing two myeloma-derived light chains and of monovalent antibody molecules containing one myeloma-derived light chain and one specific light chain (after this elution the column is suitable for reuse). Fractions containing the various materials are collected by monitoring the $OD_{280}$ using a LKB Uvichord and are dialysed firstly against five times normal strength PBS and then against normal strength PBS. The protein concentration of the dialysates is measured via the $OD_{280}$, the various preparations are tested as described below, and the preparation containing the monovalent antibodies is either stored in PBS containing 0.1% $NaN_3$ and 0.5% BSA or concentrated by ultrafiltration either for storage frozen in PBS containing 0.1% $NaN_3$ or for direct use.

The differing fractions from the column are tested simultaneously for the agglutination of mouse erythrocytes and for binding to mouse red blood cells (RBC) in a solid phase enzyme linking binding assay (SPELBA). The material not bound to the column (the breakthrough material) is typically found to be reduced in both agglutinating and binding activity compared to the whole YBM 34.3.6 monoclonal antibody preparation demonstrating that the active part of this preparation has been absorbed onto the gel. The material eluted at a pH of 4.0 typically shows strong agglutination and binding and may be assumed to contain aggregated antibody and bivalent antibody containing two specific light chains, this material having been found at low affinity and eluted owing to the lower pH and higher salt concentration of the first eluant as compared with the double strength PBS used to prepare the column. The material eluted at a pH of 2.5 typically shows the properties expected of a monovalent IgG, the proportion of bivalent antibodies present being estimated by an abolition of agglutination procedure as less than 1 part in 128. Very weak agglutination of RBC is observed for the preparation with a prozone (no agglutination) at saturation and high binding in the SPELBA test. This weak agglutination is abolished by centrifugation at 120,000 g for 5 minutes, using a Beckman airfuge, with no alteration of the antibody titre.[2]

[2]With those monoclonal antibodies which precipitate on centrifuging at 100,000 g, an alternative method of removing the remaining agglutination is employed.

PREPARATION OF MRC-OX12-SEPHAROSE GEL

The hybridoma designated MRC-OX12 is prepared by the fusion of the NS1/1-Ag4-1 myeloma and spleen cells from Balb b mice as described by Hunt and Fowler in Cell Tissue Kinetics, 1981, 14, 445. For the production of MRC-OX12 monoclonal antibodies the cells of the hybridoma MRC-OX12 are cultured by substantially the same procedure as that described by Hoang et al for the hybridoma YBM 34.3.6.

The cell-free culture supernatant obtained as above is affinity purified using a column of Sepharose to which is coupled with cyanogen bromide a mixture of normal rat IgG and of a gamma 2A- and a gamma 2C- producing monoclonal antibody, both of which are obtained from hybridomas produced by a Y3/Ag 1.2.3 - rat spleen cell fusion. The MRC-OX12 antibody is eluted with 0.1M glycine/HCl of pH 2.5 and dialysed into normal strength PBS. The dialysed product is concentrated by ultrafiltration to 2 mg/ml concentration and dialysed into 0.1M bicarbonate buffer of pH 8.6 containing 0.5M NaCl. This material is coupled at 2 mg/ml to cyanogen bromide-activated Sepharose (marketed in activated form by Pharmacia) containing 0.5 mg/ml BSA carrier, for a final ratio of 10 mg protein per gram of dry Sepharose. The coupling is effected by the manufacturer's recommended route which involves swelling and washing the gel with $10^{-3}$ HCl, incubation of the protein with the gel for 3 hours at room temperature with mixing by rotation, followed by overnight incubation with 1M ethanolamine of pH 8.3 and finally washing in 3 cycles of pH 8 buffer and then pH 4 buffer. The MRC-OX12 coupled Sepharose is stored at 4° C. with 0.1% $NaN_3$, 1% BSA in normal strength PBS and is washed with 0.2M glycine/HCl of pH 2.5, followed by normal strength PBS, before use.

EXAMPLE 2

Preparation of Monovalent Antibodies against a T-Cell Antigen

The hybridoma designated YTH 12.5.22 is prepared by the fusion of the rat myeloma line Y3/Ag 1.2.3 and spleen cells from DA rats immunised with human T-cells in an analogous procedure to that used in Example 1 for the preparation of the hybridoma YBM 34.3.6. For the production of a mixture of forms of YTH 12.5.22 monoclonal antibodies (IgG2b isotype), which bind to human T cells (reacting with a determinant of the T3 molecule) but not B cells, cells of the hybridoma YTH 12.5.22 are cultured in an analogous procedure to that used in Example 1 for the culture of the YBM 34.3.6 hybridoma but growing the cells to confluency in IMDM supplemented with 5% v/v foetal calf serum (FCS).

The spent culture supernatant is treated by affinity chromatography on Sepharose gel carrying MRC-OX12 monoclonal antibody by the same method as described in Example 1 for the YBM 34.3.6 antibodies to give a monoclonal antibody preparation enhanced in monovalent YTH 12.5.22 antibodies.

EXAMPLE 3

Preparation of Monovalent Antibodies against Glycophorin-A

The hybridoma designated YTH 89.1.8 is prepared by the fusion of the rat myeloma line Y3-Ag 1.2.3 and immune spleen cells from DA rats in an analogous procedure to that used in Example 1 for the preparation of the hybridoma YBM 34.3.6, this hybridoma being obtained from the same fusion which yields the hybridoma YTH 12.5.22 of Example 2. For the production of a mixture of forms of YTH 89.1.8 monoclonal antibodies (IgG2b isotype), which bind to the glycophorin A molecule and are able to lyse human red cells with autologous complement, cells of the hybridoma YTH 89.1.8 are cultured in an analogous procedure to that used in Example 1 for the culture of the YBM 34.3.6 hybridoma.

The spent culture supernatant is treated by affinity chromatography on Sepharose gel carrying MRC-OX12 monoclonal antibody by the same method as described in Example 1 for the YBM 34.3.6 antibodies to give a monoclonal antibody preparation enhanced in monovalent YTH 89.1.8 antibodies. These monovalent antibodies were at least as effective as killing human red cells with complement and showed increased saturation binding and loss of (weak) agglutinating activity.

EXAMPLE 4

Use of Monovalent Monoclonal Antibodies against a Blood Cell Antigen for the Quantitation of Antigen Expression on Bone Marrow Cells by Cytofluorographic Analysis A monovalant YBM 34.3.6 monoclonal antibody preparation obtained as described in Example 1 is concentrated to 250 µg per ml by ultrafiltration and is coupled to biotin succinimide ester at 100 µg per ml of antibody preparation by the following procedure.[(3)] A preparation of the antibody (which does not contain BSA) in PBS is dialysed into 0.1M bicarbonate buffer of pH 8.3, the biotin succinimide ester is added in dry dimethylformamide and the mixture is dialysed back into PBS. The resulting biotinylated antibody preparation is centrifuged at 100,000 g for 5 minutes using a Beckman airfuge and 200 µl of the separated product in HEPES buffered Eagles' medium (EH), 0.5% BSA, 0.2% $NaN_3$ and 5% heat inactivated normal rabbit serum (HINRS), at a level of 250 µg antibody per ml of medium, are added to $2 \times 10^7$ cells from whole mouse bone marrow (not KBC deleted). After incubating at 4° C. for 90 minutes, with shaking every 15 minutes, the cells are washed in the same medium, centrifuged down and 2 ml of avidin - fluorescein isothiocyanate (50 µg/ml; Sigma) are added to the cell pellet resuspended in the same medium. The cells are incubated at 4° C. for 30 minutes, with gentle agitation to prevent settling and agglutination, and the reaction is then stopped by the addition of 8 ml of the biotin-containing medium, Iscove's Modified Dulbecco's Medium (IMDM). The cells are washed in heat inactivated SIMDM (IMDM in which the bicarbonate buffer is replaced by NaCl - buffered to pH 7.2) 0.5% BSA, 0.2% $NaN_3$ containing 50 µg per ml of propidium iodide and are then suspended in phenol red free medium for cell sorting.

[(3)]As biotinylated YBM 34.3.6 antibody is not bound by MRC-OX12 antibody, affinity purification of the monovalent antibody must precede biotinylation.

The use of a monovalent monoclonal antibody preparation as described above typically gives no agglutinates of more than four cells on observation under a microscope but ensures an excess of all the reagents and saturation binding. A four parameter analysis was performed on the samples using an Ortho HSO Computer Controlled Cytofluorograf at 2,000 cells per second. Typical figures for the cell differential counts and recoveries obtained in the sorted fractions after cytocentrifuge preparations and May-Grünwalds and Giemsa stains had been performed are presented in the Table. The distribution of cells between the three sorted fractions based on fluorescence is shown for erythroblasts (basophili cells with nucleoli), maturing normoblasts (condensed nucleus and degrees of oxyphilic staining) and erythrocytes or RBC, these representing the three main divisions of morphological differentation in the erythroid series. The calculated mean and standard deviation for each cell type is given beneath the distribution figures.

It will be seen from the Table that the antigen against which the YBM 34.3.6 antibody is directed is expressed weakly on the majority of erythroblasts (69% of the cells have a mean fluorescence of $57 \pm 24$) but a smaller proportion appear strongly positive (25% having a mean of $737 \pm 311$) which raises the overall means to $231 \pm 113$. Normoblasts show the highest level of fluorescence ($528 \pm 217$), whilst mature RBC have an intermediate level of antigen expression (means $212 \pm 67$).

Figure 1:
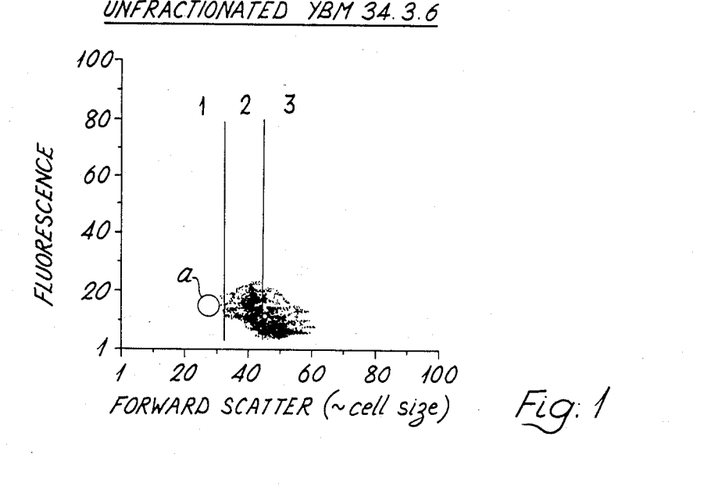
Figure 2:
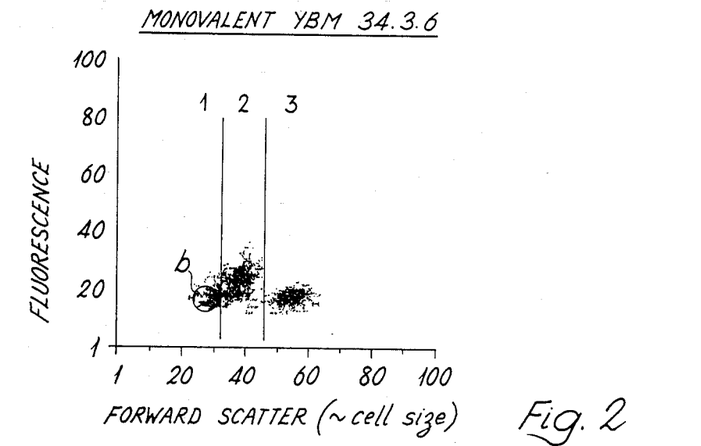

The accompanying FIGS. 1 and 2 illustrate the improvement obtained with the monovalent antibody preparation as compared with a similar formulation of a YBM 34.3.6 monoclonal antibody mixture which has not been fractionated.

Each figure consists of a cytogram showing forward scatter (approximating to cell size) on the x axis and fluorescence on the y axis with each dot plotted on the x,y coordinates representing the measurements obtained for a single cell as it passes through the cell sorter's laser beam (area 1 corresponds to red cells, area 2 to lymphocytes/nucleated red cells and area 3 to myclomonocytic cells). It will be seen that the monovalent YBM 34.3.6 preparation gives a cytogram showing a marked improvement in the resolution of the different cell populations in the bone marrow and also retains the smaller red cells which are lost through agglutination by divalent antibody (compare the enclosed regions a and b of FIGS. 1 and 2, the loss in area a being evident).

TABLE

| Monoclonal antibody | Channels | FITC | CELL MORPHOLOGY % (recovery %) | | | | | | | Sorted % |
|---|---|---|---|---|---|---|---|---|---|---|
| | | | Erythro-blast | Normo-blast | RBC | Blast Myelo-blast | Mono-cytes | Meta-myelo-cytes, PMN | Lympho-cytes | |
| Bone marrow control | unsorted | | 14 | 12 | 16 | 7 | 4 | 34 | 14 | 100 |
| YBM 34.3.6 mono total | unsorted | | 12 | 14 | 26 | 4 | 1 | 28 | 16 | 100 |
| YBM 34.3.6 mono ++ | 201–1000 | 737 ± 311 | 11(25) | 38(67) | 6(13) | 2(33) | 0(0) | 20(18) | 23(44) | 36 |
| YBM 34.3.6 mono + | 100–199 | 138 ± 29 | 7(6) | 20(19) | 66(81) | 1(0) | 1(0) | 3(3) | 5(6) | 20 |

TABLE-continued

| Monoclonal antibody | Channels | FITC | CELL MORPHOLOGY % (recovery %) | | | | | | | |
|---|---|---|---|---|---|---|---|---|---|---|
| | | | Erythro-blast | Normo-blast | RBC | Blast Myelo-blast | Mono-cytes | Meta-myelo-cytes, PMN | Lympho-cytes | Sorted % |
| YBM 34.3.6 mono '—' | 1–99 | 57 ± 24 | 20(69) | 6(14) | 2(7) | 3(67) | 3(100) | 52(79) | 16(50) | 58 |
| Total recovery | 1–1000 | — | 14 | 18 | 14 | 3 | 2 | 33 | 16 | 100 |
| Mean fluorescence | — | — | 231 ± 133 | 528 ± 217 | 212 ± 67 | 281 ± 118 | 57 ± 24 | 181 ± 75 | 361 ± 75 | — |

EXAMPLE 5

Use of Monovalent Monoclonal Antibodies against a T-Cell Antigen to improve Cytotoxicity with Complement The cytotoxic properties of the monovalent YTH 12.5.22 preparation obtained as described in Example 2 were compared as follows with those of antibody obtained from the untreated cell-free culture supernatant referred to in Example 2 by a conventional precipitation procedure using 50% w/v saturated ammonium sulphate. The two antibody preparations, each at 150 μg/ml in PBS, were titrated in culture medium (SIMDM+5% FCS) with $^{51}$Cr labelled human peripheral blood lymphocytes (PBL) obtained from defibrinated venous blood with the red blood cells removed by centrifugation on Ficoll-Hypaque. After 30 minutes incubation at room temperature, rabbit or human serum complement in SIMDM+5% FCS was added to a final dilution of 1/10 and incubation was continued for 60 minutes at 37° C. The cells were then pelleted and the supernatants were removed for gamma counting.

Figure 3:
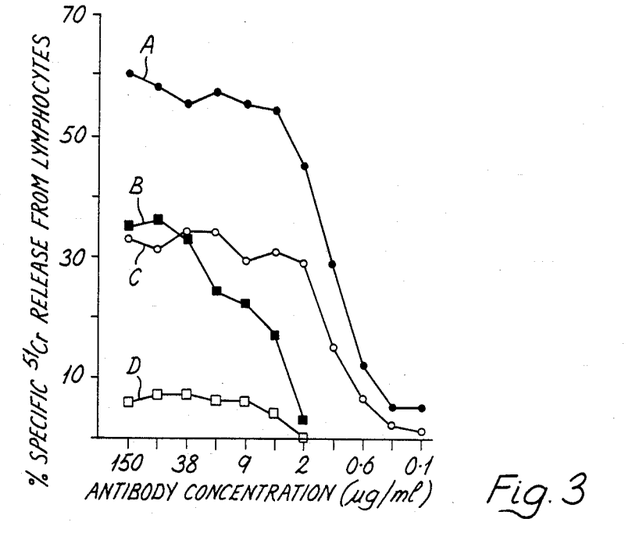

In the accompanying FIG. 3, the specific killing of cells, as measured by the $^{51}$Cr release from lymphocytes, is shown for the two antibody preparations described above, as compared to a reference standard. The reference standard used was a preparation at 50 μg/ml of the monoclonal antibodies CAMPATH 1 (Cobbold et al, ibid) which kill all lymphocytes, both T and also B cells, and the values shown for specific $^{51}$Cr release are related to a value of 100% obtained with this reference standard. The plots are labelled A, B, C and D for monovalent IgG (rabbit complement), supernatant IgG (rabbit complement), monovalent IgG (human complement) and supernatant IgG (human complement), respectively. It will be seen that cytoxicity is markedly increased for the monovalent YTH 12.5.22 preparation as compared with an unfractionated preparation when either human or rabbit complement was used.

EXAMPLE 6

Comparison of Activity of Monovalent Monoclonal Antibody Preparations containing Varying Proportions of Monovalent Antibody YTH 12.5.22 monovalent and supernatant Ig were obtained essentially as described in Example 2. The monovalent and unfractionated supernatant preparations and mixtures thereof in various proportions, were tested for their ability to kill peripheral blood lymphocytes as described in Example 5, titrating with $^{51}$Cr labelled lymphocytes starting at a total Ig concentration of approximately 20 μg/ml and using human serum complement rather than rabbit complement. The approximate proportions of monovalent:bivalent material in each preparation were estimated using the ELISA assays described by Cobbold and Waldmann, Nature, 1984, 308, 460–462. The supernatant of YTH 12.5.22 contained about 15–20% of the antigen binding activity in the monovalent form (which is less than is usually the case), while bivalent material was undetectable in the fractionated Ig.

Figure 4:
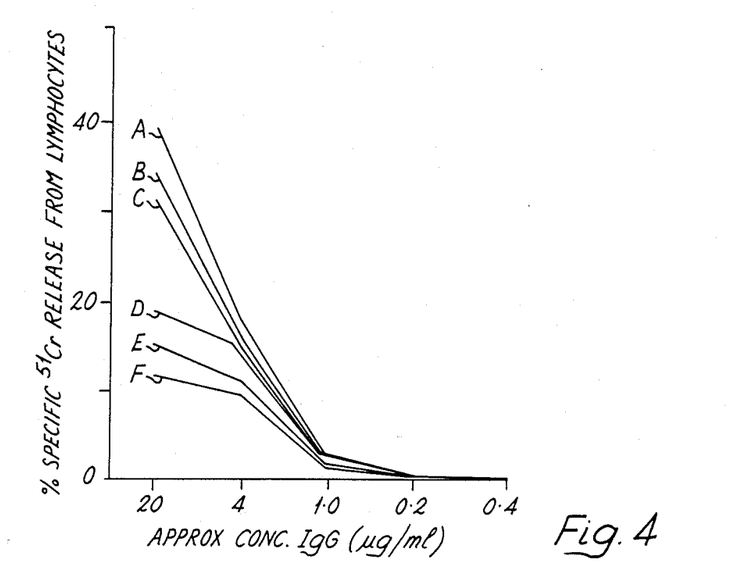

The results obtained are expressed in FIG. 4 in a similar manner to that used in FIG. 3, the plot labelled A corresponding to the monovalent preparation of Example 2 assayed as containing no detectable bivalent antibodies (>100:1 ratio of monovalent to bivalent antibody) and the plot labelled F corresponding to the unfractionated supernatant assayed as containing a <1:1 ratio of monovalent to bivalent antibodies, whilst plots B to E correspond to intermediate ratios of monovalent to bivalent antibody produced by mixing, which ratios are estimated as follows:

| | |
|---|---|
| A | >100:1 |
| B | 25:1 |
| C | 7:1 |
| D | 3:1 |
| E | 2:1 |
| F | <1:1 |

It will be seen that, in the case of YTH 12.5.22, monovalent: bivalent ratios in excess of 7:1 gave significant improvement of killing, but that the most effective lysis was obtained with the preparation containing no detectable bivalent material.

We claim:

1. A monoclonal antibody preparation, comprising intact IgG antibody molecules having a single binding activity, which activity is in respect of a cell surface antigen of a target cell, and having only one of the two light chains which will bind to the antigen, the other non-binding light chain being characteristic of a cell not specifically to the antigen from which the source hybridoma derives, the proportion of such antibody molecules relative to IgG antibody molecules having two light chains which will bind to the antigen being about 10:1 or more to thereby produce an enhancement of the binding activity of the mixture of the antibody molecules as originally secreted.

2. A monoclonal antibody preparation, comprising intact IgG antibody molecules having a single binding activity, which activity is in respect of a cell surface antigen of a target cell, and having only one of the two light chains which will bind to the antigen, the other non-binding light chain being characteristic of a cell not specifically to the antigen from which the source hybridoma derives, said intact IgG antibody molecules being in an enhanced proportion of from about 10:1 to 1000:1 relative to IgG antibody molecules in which both light chains will bind to the antigen.

3. A monoclonal antibody preparation according to claim 1, in which said proportion is 100:1 or more.

4. A monoclonal antibody preparation according to claim 2, in which said proportion is 100:1 or more.

5. A monoclonal antibody preparation according to claim 1, in which the IgG antibody molecules in which only one of the two light chains will bind to the antigen are substantially free from IgG antibody molecules in which neither light chain will bind to the antigen.

6. A monoclonal antibody preparation having activity against a cell surface antigen of a target cell, said preparation comprising intact IgG antibody molecules having two identical heavy chains specific for the antigen, a first light chain specific for the antigen and a second light chain which is non-specific for the antigen and which is characteristic of a cell not specifically to the antigen from which the source hybridoma derives, the proportion of such antibody molecules relative to IgG antibody molecules having two of said heavy chains and two of said first light chains specific for the antigen being about 10:1 or more to thereby produce an enhancement of the binding activity of the mixture of the antibody molecules as originally secreted.

7. A monoclonal antibody preparation having activity against a cell surface antigen of a target cell, said preparation comprising intact IgG antibody molecules having two identical heavy chains specific to the antigen, a first light chain specific for the antigen and a second light chain which is non-specific to the antigen and which is characteristic of a cell not specifically to the antigen from which the source hybridoma derives, the proportion of such antibody molecules relative to IgG antibody molecules having two of said heavy chains and two of said first light chains specific for the antigen being about 10:1 to 1000:1.

8. A monoclonal antibody preparation according to claim 6, in which the proportion is 100:1 or more.

9. A monoclonal antibody preparation according to claim 7, in which the proportion is 100:1 or more.

10. A monoclonal antibody preparation according to claim 6, in which the IgG antibody molecules having two identical heavy chains specific for said antigen, a first light chain specific for said antigen and a second light chain which is non-specific for said antigen, are substantially free from IgG antibody molecules having two of said heavy chains specific for the antigen and two of said second light chains non-specific for the antigen.

11. A monoclonal antibody preparation according to claim 6, in which the preparation derives from a hybridoma produced by a fusion involving a myeloma which will impart to the hybridoma a light chain characteristic of the myeloma.

12. A monoclonal antibody preparation according to claim 1, in which the preparation is active against an antigen on the surface of a blood cell.

13. A monoclonal antibody preparation according to claim 12, in which the blood cell is a lymphocyte.

14. A monoclonal antibody preparation according to claim 1, in which the preparation is active against an antigen associated with the surface of neoplastic cells.

15. A monoclonal antibody preparation according to claim 6, in which the first and second light chains are serologically distinct.

* * * * *

UNITED STATES PATENT AND TRADEMARK OFFICE
CERTIFICATE OF CORRECTION

| | |
|---|---|
| PATENT NO. : | 4,841,025 |
| DATED : | June 20, 1989 |
| INVENTOR(S) : | COBBOLD et al |

It is certified that error appears in the above-identified patent and that said Letters Patent is hereby corrected as shown below:

Front page after heading "Related U.S. Application Data" add:

--[30]  Foreign Application Priority Data
            July 8, 1983 [GB] United Kingdom....8318575--

Column 14 line 51 insert --sensitized-- after "specifically"

Column 14 line 64 insert --sensitized-- after "specifically"

Column 15 line 16 insert --sensitized-- after "specifically"

Column 15 line 30 insert --sensitized-- after "specifically"

Signed and Sealed this

Tenth Day of April, 1990

*Attest:*

HARRY F. MANBECK, JR.

*Attesting Officer*   *Commissioner of Patents and Trademarks*